United States Patent
Qian et al.

(10) Patent No.: US 7,259,289 B2
(45) Date of Patent: Aug. 21, 2007

(54) MCH1R DEFICIENT MICE

(75) Inventors: Su Qian, Edison, NJ (US); Donald J. Marsh, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 270 days.

(21) Appl. No.: 10/472,629

(22) PCT Filed: Mar. 19, 2002

(86) PCT No.: PCT/US02/08413

§ 371 (c)(1),
(2), (4) Date: Sep. 19, 2003

(87) PCT Pub. No.: WO02/077168

PCT Pub. Date: Oct. 3, 2002

(65) Prior Publication Data

US 2004/0128708 A1    Jul. 1, 2004

Related U.S. Application Data

(60) Provisional application No. 60/278,061, filed on Mar. 22, 2001.

(51) Int. Cl.
*A01K 67/027* (2006.01)
*G01N 33/00* (2006.01)
(52) U.S. Cl. ............... 800/18; 800/3; 800/8; 800/9; 800/14
(58) Field of Classification Search .............. 800/18, 800/3, 8, 9, 14
See application file for complete search history.

(56) References Cited

U.S. PATENT DOCUMENTS

| | | | |
|---|---|---|---|
| 5,654,182 | A | 8/1997 | Whal et al. |
| 6,127,598 | A | 10/2000 | German et al. |
| 6,136,040 | A | 10/2000 | Ornitz et al. |
| 6,147,275 | A | 11/2000 | Vale et al. |
| 6,150,365 | A | 11/2000 | Mayol |
| 6,166,287 | A | 12/2000 | Vale et al. |
| 6,221,613 | B1 | 4/2001 | Salon et al. |
| 6,221,616 | B1 | 4/2001 | Salon et al. |
| 6,291,195 | B1 | 9/2001 | Salon et al. |

FOREIGN PATENT DOCUMENTS

| | | |
|---|---|---|
| WO | WO 00/39279 | 7/2000 |
| WO | WO 00/49170 | 8/2000 |
| WO | WO 01/05947 | 1/2001 |
| WO | WO 01/68706 | 9/2001 |

OTHER PUBLICATIONS

Marsh DJ, Melanin-concentrating hormone 1 receptor-deficient mice are lean, hyperactive, and hyperphagic and have altered metabolism, 2002, PNAS, vol. 99, pp. 3240-3245.*

Concalves M, A concise peer into the background, initial thoughts, and practices of human gene therapy, 2005, BioEssays, vol. 27, pp. 506-517.*
Parekh-Olmedo H, Gene therapy progress and prospects: targeted gene repair, 2005, Gene Therapy, vol. 12, pp. 639-646.*
Verma IM, Gene Therapy: Twenty-first century medicine, 2005, Annu. Rev. Biochem. vol. 74, pp. 711-738.*
Ausubel, F. et al. "Manipulating the Mouse Genome", Current Protocols in Molecular Biology, John Wiley & Sons, Inc., 2001, Chapter 23.
Bachner, D. et al. "Identification of melanin concentrating hormone (MCH) as the natural ligand for the orphan somatostatin-like receptor 1 (SLC-)", FEBS Letters, 1999, vol. 457, pp. 522-524.
Bluet-Pajot, M. et al. "Neuropeptide-E-1 Antagonizes the Action of Melanin-Concentrating Hormone on Stress-Induced Release of Adrenocorticotropin in the Rat", Journal of Neuroendocrinology, 1995, vol. 7, pp. 297-303.
Breton, C. et al. "Isolation and characterization of the human melanin-concentrating hormone gene and a variant gene", Molecular Brain Research, 1993, vol. 18, pp. 297-310.
Chambers, J. et al. "Melanin-concentrating hormone is the cognate ligand for the orphan G-protein-coupled receptor SLC-1", Nature, 1999, vol. 400, pp. 261-265.
Chen, A. et al. "Inactivation of the mouse melanocortin-3 receptor results in increased fat mass and reduced lean body mass", Nature Genetics, 2000, vol. 26, pp. 97-102.
Chen, A. et al. "Role of the melanocortin-4 receptor in metabolic rate and food intake in mice", Transgenic Research, 2000, vol. 9, pp. 145-154.
Drozdz, R. et al. "Characterization of the Receptor for Melanin-Concentrating Hormone on Melanoma Cells by Photocrosslinking", Annals New York Academy of Sciences, 1999, pp. 210-213.
Flier, J. et al. "Obesity and the Hypothalamus: Novel Peptides for New Pathways", Cell, 1998, vol. 92, pp. 437-440.
Kawauchi, H. et al. "Characterization of malanin-concentrating hormone in chum salmon pituitaries", Nature, 1983, vol. 305, pp. 321-323.
Kennedy, A. et al. "Melanin-Concentrating Hormone (MCH) Suppresses Thyroid Stimulating Hormone (TSH) release, in vivo and in vitro, via the Hypothalamus and the Pituitary", Endocrinology, 2000, vol. 142, pp. 3265-3268.
Knigge, K. et al. "Melanotropic Peptides in the Mammalian Brain: The Melanin-Concentrating Hormone", Peptides, 1996, vol. 17, pp. 1063-1073.

(Continued)

*Primary Examiner*—Sumesh Kaushal
*Assistant Examiner*—David A. Montanari
(74) *Attorney, Agent, or Firm*—Catherine D. Fitch; Sheldon O. Heber

(57) ABSTRACT

The present invention features viable MCH1R deficient mice. MCH1R deficient mice contain an alteration in one or both MCH1R alleles that substantially reduces expression of a functional MCH1R from the altered allele. Preferably, MCH1R deficient mice are MCH1R –/– knockout mice.

10 Claims, 5 Drawing Sheets

OTHER PUBLICATIONS

Lakaye, B. et al. "Cloning of the rat brain cDNA encoding for the SLC-1 G protein coupled receptor reveals the presence of an intron in the gene", Biochimica et Biophysica Acta, 1998, vol. 1401, pp. 216-220.

Ludwig, D. et al. "Melanin-concentrating hormone overexpression in transgenic mice leads to obesity and insulin resistance", The Journal of Clinical Investigation, 2001, vol. 107, pp. 379-386.

MacDonald, D. et al. "Molecular Characterization of the Melanin-Concentrating Hormone/Receptor Complex: Identification of Critical Residues Involved in Binding and Activation", Molecular Pharmacology, 2000, vol. 58, pp. 217-225.

Nahon, J. "The Melanin-Concentrating Hormone: From the Peptide to the Gene", Critical Reviews in Neurobiology 1994, vol. 8, pp. 221-262.

Nothacker, H. et al. "Identification of the natural ligand of an orphan G-protein-coupled receptor involved in the regulation of vasoconstriction", Nature Cell Biology, 1999, vol. 1, pp. 383-385.

Presse, F. et al. "Structure of the Human Melanin Concentrating Hormone mRNA", Molecular Endocrinology, 1990, vol. 4, pp. 632-637.

Qu, D. et al. "A role for melanin-concentrating hormone in the central regulation of feeding behaviour", Nature, 1996, vol. 380, pp. 243-247.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Spiegelman, B. et al. "Obesity and the Regulation of Energy Balance", Cell, 2001, vol. 104, pp. 531-543.

Marsh, D. et al. "Melanin-concentrating hormone 1 receptor-deficient mice are lean, hyperactive, and hyperphagic and have altered metabolism", Proc. Nat. Acad. Sci. USA, 2002, vol. 99, pp. 3240-3425.

* cited by examiner

SEQUENCE LISTING

<160> NUMBER OF SEQ ID NOS: 11

<210> SEQ ID NO 1
<211> LENGTH: 353
<212> TYPE: PRT
<213> ORGANISM: Human

<400> SEQUENCE: 1

Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
            20                  25                  30

-continued

```
Thr Gly Ser Ile Ser Tyr Ile Asn Ile Ile Met Pro Ser Val Phe Gly
            35                  40                  45
Thr Ile Cys Leu Leu Gly Ile Gly Asn Ser Thr Val Ile Phe Ala
 50                  55                  60
Val Val Lys Lys Ser Lys Leu His Trp Cys Asn Asn Val Pro Asp Ile
 65                  70                  75                  80
Phe Ile Ile Asn Leu Ser Val Val Asp Leu Leu Phe Leu Leu Gly Met
                85                  90                  95
Pro Phe Met Ile His Gln Leu Met Gly Asn Gly Val Trp His Phe Gly
               100                 105                 110
Glu Thr Met Cys Thr Leu Ile Thr Ala Met Asp Ala Asn Ser Gln Phe
               115                 120                 125
Thr Ser Thr Tyr Ile Leu Thr Ala Met Ala Ile Asp Arg Tyr Leu Ala
           130                 135                 140
Thr Val His Pro Ile Ser Ser Thr Lys Phe Arg Lys Pro Ser Val Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
               180                 185                 190
Gly Cys Gly Ile Arg Leu Pro Asn Pro Asp Thr Asp Leu Tyr Trp Phe
           195                 200                 205
Thr Leu Tyr Gln Phe Phe Leu Ala Phe Ala Leu Pro Phe Val Val Ile
   210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
               260                 265                 270
Tyr Val Leu Gln Leu Thr Gln Leu Ser Ile Ser Arg Pro Thr Leu Thr
           275                 280                 285
Phe Val Tyr Leu Tyr Asn Ala Ala Ile Ser Leu Gly Tyr Ala Asn Ser
   290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Ala
                325                 330                 335
Val Ser Asn Ala Gln Thr Ala Asp Glu Glu Arg Thr Glu Ser Lys Gly
               340                 345                 350
Thr
```

<210> SEQ ID NO 2
<211> LENGTH: 1062
<212> TYPE: DNA
<213> ORGANISM: Human

<400> SEQUENCE: 2

```
atggacctgg aagcctcgct gctgcccact ggtcccaacg ccagcaacac ctctgatggc    60
cccgataacc tcacttcggc aggatcacct cctcgcacgg ggagcatctc ctacatcaac   120
atcatcatgc cttcggtgtt cggcaccatc tgcctcctgg gcatcatcgg aactccacg   180
gtcatcttcg cggtcgtgaa gagtccaag ctgcactggt gcaacaacgt ccccgacatc    240
ttcatcatca acctctcggt agtagatctc ctctttctcc tgggcatgcc cttcatgatc   300
```

-continued

```
caccagctca tgggcaatgg ggtgtggcac tttggggaga ccatgtgcac cctcatcacg   360
gccatggatg ccaatagtca gttcaccagc acctacatcc tgaccgccat ggccattgac   420
cgctacctgg ccactgtcca ccccatctct ccacgaagt tccggaagcc ctctgtggcc    480
accctggtga tctgcctcct gtgggccctc tccttcatca gcatcacccc tgtgtggctg   540
tatgccagac tcatcccctt ccaggaggt gcagtgggct gcggcatacg cctgcccaac    600
ccagacactg acctctactg gttcaccctg taccagtttt tcctggcctt tgccctgcct   660
tttgtggtca tcacagccgc atacgtgagg atcctgcagc gcatgacgtc ctcagtggcc   720
cccgcctccc agcgcagcat ccggctgcgg acaaagaggg tgacccgcac agccatcgcc   780
atctgtctgg tcttctttgt gtgctgggca ccctactatg tgctacagct gacccagttg   840
tccatcagcc gcccgaccct cacctttgtc tacttataca atgcggccat cagcttgggc   900
tatgccaaca gctgcctcaa ccccttttgtg tacatcgtgc tctgtgagac gttccgcaaa   960
cgcttggtcc tgtcggtgaa gcctgcagcc caggggcagc ttcgcgctgt cagcaacgct   1020
cagacggctg acgaggagag gacagaaagc aaaggcacct ga                      1062
```

<210> SEQ ID NO 3
<211> LENGTH: 340
<212> TYPE: PRT
<213> ORGANISM: Human

<400> SEQUENCE: 3

Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

```
Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340

<210> SEQ ID NO 4
<211> LENGTH: 1023
<212> TYPE: DNA
<213> ORGANISM: Human

<400> SEQUENCE: 4
atgaatccat tcatgcatc  ttgttggaac  acctctgccg  aacttttaaa  caaatcctgg         60
aataaagagt tgcttatca  aactgccagt  gtggtagata  cagtcatcct  cccttccatg        120
attgggatta tctgttcaac agggctggtt  ggcaacatcc  tcattgtatt  cactataata        180
agatccagga aaaaaacagt ccctgacatc  tatatctgca  acctggctgt  ggctgatttg        240
gtccacatag ttggaatgcc ttttcttatt  caccaatggg  cccgaggggg  agagtgggtg        300
tttgggggc  ctctctgcac catcatcaca  tccctggata  cttgtaacca  atttgcctgt        360
agtgccatca tgactgtaat gagtgtggac  aggtactttg  ccctcgtcca  accatttcga        420
ctgacacgtt ggagaacaag gtacaagacc  atccggatca  atttgggcct  tgggcagct        480
tcctttatcc tggcattgcc tgtctgggtc  tactcgaagg  tcatcaaatt  taaagacggt        540
gttgagagtt gtgcttttga tttgacatcc  cctgacgatg  tactctggta  tacactttat        600
ttgacgataa caactttttt ttccctcta   cccttgattt  tggtgtgcta  tattttaatt        660
ttatgctata cttgggagat gtatcaacag  aataaggatg  ccagatgctg  caatcccagt        720
gtaccaaaac agagagtgat gaagttgaca  aagatggtgc  tggtgctggt  ggtagtcttt        780
atcctgagtg ctgccccta  tcatgtgata  caactggtga  acttacagat  ggaacagccc        840
acactggcct tctatgtggg ttattacctc  tccatctgtc  tcagctatgc  cagcagcagc        900
attaacccct tctctctacat cctgctgagt  ggaaatttcc  agaaacgtct  gcctcaaatc        960
caaagaagag cgactgagaa ggaaatcaac  aatatgggaa  acactctgaa  atcacacttt       1020
tag                                                                        1023

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 5
aaattgctag ggaggcttgc ag                                                     22
```

```
<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 6
taaagcgcat gctccagact gcctt                                       25

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 7
ttaaaggaac ccaagctagg cacc                                        24

<210> SEQ ID NO 8
<211> LENGTH: 45
<212> TYPE: DNA
<213> ORGANISM: Artificial Sequence
<220> FEATURE:
<223> OTHER INFORMATION: Oligonucleotide probe

<400> SEQUENCE: 8
ctaatgaacg agagagccca caggaggcag atcaccaggg tggcc                 45

<210> SEQ ID NO 9
<211> LENGTH: 45
<212> TYPE: DNA
<213> ORGANISM: Artificial Sequence
<220> FEATURE:
<223> OTHER INFORMATION: Oligonucleotide probe

<400> SEQUENCE: 9
ccagcacaca aagaagacca gacagatggc aatggctgtg cgggt                 45

<210> SEQ ID NO 10
<211> LENGTH: 1999
<212> TYPE: DNA
<213> ORGANISM: Artificial Sequence
<220> FEATURE:
<223> OTHER INFORMATION: Mouse cDNA encoding MCH1R
<220> FEATURE:
<221> NAME/KEY: CDS
<222> LOCATION: (138)...(1199)

<400> SEQUENCE: 10
ggcggtagag gaagacccctt ttctggactg cggggctcaa gctccggaca aggcggtgga    60
gggcgctgga ggctgccgca gcctgcgtgg gtggacgggc gctccactcc agggagcagg   120
cgacctgcac cggctgc atg gat ctg caa gcc tcg ttg ctg tcc act ggc      170
                Met Asp Leu Gln Ala Ser Leu Leu Ser Thr Gly
                  1               5                  10 ccc aat gcc agc aac atc tcc gat ggc cag gat aat ttc aca ttg gcg    218
Pro Asn Ala Ser Asn Ile Ser Asp Gly Gln Asp Asn Phe Thr Leu Ala
             15                  20                  25 ggg cca cct cct cgc aca agg agt gtc tcc tac atc aac atc atc atg    266
Gly Pro Pro Pro Arg Thr Arg Ser Val Ser Tyr Ile Asn Ile Ile Met
 30                  35                  40 cct tca gtg ttt ggt acc atc tgt ctc ctg ggc att gtg gga aac tcc    314
Pro Ser Val Phe Gly Thr Ile Cys Leu Leu Gly Ile Val Gly Asn Ser
 45                  50                  55
```

```
aca gtc att ttt gcc gtg gtg aag aaa tcc aag ctg cac tgg tgc agc      362
Thr Val Ile Phe Ala Val Val Lys Lys Ser Lys Leu His Trp Cys Ser
 60              65                  70                  75 aac gtc cct gac atc ttc atc atc aac ctc tct gtg gtg gat ctg ctt      410
Asn Val Pro Asp Ile Phe Ile Ile Asn Leu Ser Val Val Asp Leu Leu
                 80                  85                  90 ttc ctg ctg ggc atg cct ttc atg atc cac cag ctc atg ggt aat ggt      458
Phe Leu Leu Gly Met Pro Phe Met Ile His Gln Leu Met Gly Asn Gly
             95                 100                 105 gtc tgg cac ttt ggg gaa acc atg tgc acc ctc atc aca gcc atg gac      506
Val Trp His Phe Gly Glu Thr Met Cys Thr Leu Ile Thr Ala Met Asp
        110                 115                 120 gcc aac agt cag ttc acc agc acc tac atc ctg act gct atg gcc att      554
Ala Asn Ser Gln Phe Thr Ser Thr Tyr Ile Leu Thr Ala Met Ala Ile
    125                 130                 135 gac cgc tac ttg gcc acc gtc cat ccc atc tcc tcc acc aag ttc cgg      602
Asp Arg Tyr Leu Ala Thr Val His Pro Ile Ser Ser Thr Lys Phe Arg
140                 145                 150                 155 aag ccc tcc atg gcc acc ctg gtg atc tgc ctc ctg tgg gct ctc tcg      650
Lys Pro Ser Met Ala Thr Leu Val Ile Cys Leu Leu Trp Ala Leu Ser
                160                 165                 170 ttc att agc atc act cct gtg tgg ctc tat gcc agg ctt atc ccc ttc      698
Phe Ile Ser Ile Thr Pro Val Trp Leu Tyr Ala Arg Leu Ile Pro Phe
            175                 180                 185 cca ggg ggt gct gtg ggc tgt ggc atc cgc cta cca aac cca gat act      746
Pro Gly Gly Ala Val Gly Cys Gly Ile Arg Leu Pro Asn Pro Asp Thr
        190                 195                 200 gat ctt tac tgg ttc act ctg tat cag ttt ttc ctg gcc ttc gcc ctt      794
Asp Leu Tyr Trp Phe Thr Leu Tyr Gln Phe Phe Leu Ala Phe Ala Leu
    205                 210                 215 ccg ttt gtg gtc atc act gct gcg tac gtg aaa ata cta cag cgc atg      842
Pro Phe Val Val Ile Thr Ala Ala Tyr Val Lys Ile Leu Gln Arg Met
220                 225                 230                 235 acg tct tcg gtg gcc cca gcc tct caa cgc agc atc cgg ctt cgg aca      890
Thr Ser Ser Val Ala Pro Ala Ser Gln Arg Ser Ile Arg Leu Arg Thr
                240                 245                 250 aag agg gtg acc cgc aca gcc att gcc atc tgt ctg gtc ttc ttt gtg      938
Lys Arg Val Thr Arg Thr Ala Ile Ala Ile Cys Leu Val Phe Phe Val
            255                 260                 265 tgc tgg gcg ccc tac tac gtg ctg cag ctg acc cag ttg tcc atc agc      986
Cys Trp Ala Pro Tyr Tyr Val Leu Gln Leu Thr Gln Leu Ser Ile Ser
        270                 275                 280 cgc ccg acc ctc aca ttc gtc tac ctg tac aat gcg gcc atc agc ttg     1034
Arg Pro Thr Leu Thr Phe Val Tyr Leu Tyr Asn Ala Ala Ile Ser Leu
    285                 290                 295 ggc tat gcc aac agc tgc ctc aat ccc ttt gtg tac ata gta ctc tgt     1082
Gly Tyr Ala Asn Ser Cys Leu Asn Pro Phe Val Tyr Ile Val Leu Cys
300                 305                 310                 315 gag acc ttt cga aaa cgc ttg gtg ctg tcg gtg aag ccc gcg gcc cag     1130
Glu Thr Phe Arg Lys Arg Leu Val Leu Ser Val Lys Pro Ala Ala Gln
                320                 325                 330 ggg cag ctt cgc acg gtc agc aat gct cag aca gct gac gag gag agg     1178
Gly Gln Leu Arg Thr Val Ser Asn Ala Gln Thr Ala Asp Glu Glu Arg
            335                 340                 345 aca gaa agc aaa ggc acc tga caatccccc cggtcacctc caagtcaggt         1229
Thr Glu Ser Lys Gly Thr  *
                350 caccgcatca aaccatgggg agagatactg agataaaccc ggggctaccc tgggaggatg   1289
```

-continued

```
cagaagctgg aggctggggg cttgtagcaa accacattcc acggggccca caaattgcta    1349
gggaggcttg cagcctggtt tggggggaa gcctcagact gcaggatcc ccttgacaga      1409 atagaagcgg agcaagaagg aaaggtggt ttgactggtt ctcggggtct gtatctgttg    1469
gctcgcatat atctttctct caaggaaga aggcggaggt gcctagctgg gttccttaa      1529 aactaggcag ggctaggatc tgagcagcta gggctctact gtgagactgg gcaagccgag    1589
cgttccctcc catctctcat tggtgttgat agaaggcagt ctttctccca gctggtgga    1649 tctcctgaag cacgctgcct gggctccagc atcctgtgcg gatttcacgt tctctttagg   1709
ggatgcatgt tgacactggg gtgtgggctc tgagcccaca ggagtttaaa aaaccaaaag   1769
agctcagagt gtcgagagag acccaatcac cgagaatgac aaggcaacct ggggtggatg   1829
tggatcttga aactaataaa aagggttttt cacagtgaca gcgacattct cttcataggg    1889
cacagctgtc agtctatggc tgatccagag cgagcatcca tgaattctgc atgtgcaggg   1949
gtcactctaa tacctgatat gttggcatca tctttgtgct tgagccttcc              1999
```

<210> SEQ ID NO 11
<211> LENGTH: 353
<212> TYPE: PRT
<213> ORGANISM: Mouse

<400> SEQUENCE: 11

```
Met Asp Leu Gln Ala Ser Leu Leu Ser Thr Gly Pro Asn Ala Ser
  1               5                  10                  15

Ile Ser Asp Gly Gln Asp Asn Phe Thr Leu Ala Gly Pro Pro Arg
                 20                  25                  30

Thr Arg Ser Val Ser Tyr Ile Asn Ile Ile Met Pro Ser Val Phe Gly
                 35                  40                  45

Thr Ile Cys Leu Leu Gly Ile Val Gly Asn Ser Thr Val Ile Phe Ala
         50                  55                      60

Val Val Lys Lys Ser Lys Leu His Trp Cys Ser Asn Val Pro Asp Ile
 65                  70                  75                  80

Phe Ile Ile Asn Leu Ser Val Val Asp Leu Leu Phe Leu Leu Gly Met
                 85                  90                      95

Pro Phe Met Ile His Gln Leu Met Gly Asn Gly Val Trp His Phe Gly
                100                 105                 110

Glu Thr Met Cys Thr Leu Ile Thr Ala Met Asp Ala Asn Ser Gln Phe
                115                 120                 125

Thr Ser Thr Tyr Ile Leu Thr Ala Met Ala Ile Asp Arg Tyr Leu Ala
        130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
                180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
        210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
```

```
                    245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr
```

MCH1R DEFICIENT MICE

CROSS-REFERENCE TO RELATED APPLICATIONS

The present application claims priority to provisional application U.S. Ser. No. 60/278,061, filed Mar. 22, 2001, hereby incorporated by reference herein.

BACKGROUND OF THE INVENTION

The references cited in the present application are not admitted to be prior art to the claimed invention.

Neuropeptides present in the hypothalamus play a major role in mediating the control of body weight. (Flier, et al., 1998. *Cell,* 92, 437-440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632-637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi, et al., 1983. *Nature* 305, 321-323.)

In humans two genes encoding MCH have been identified that are expressed in the brain. (Breton, et al., 1993. *Mol. Brain Res.* 18, 297-310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063-1073.)

Pharmacological and genetic evidence suggest that the primary mode of MCH action is to promote feeding (orexigenic). MCH mRNA is up regulated in fasted mice and rats and in the ob/ob mouse. (Qu, et al., 1996. *Nature* 380, 243-247.) Injection of MCH centrally (ICV) stimulates food intake and MCH antagonizes the hypophagic effects seen with α melanocyte stimulating hormone (αMSH). (Qu, et al., 1996. *Nature* 380, 243-247.) MCH deficient mice are lean, hypophagic and have increased metabolic rate. (Shimada, et al., 1998. *Nature* 396, 670-673.) Transgenic mice overexpressing MCH are hyperphagic and develop insulin resistance and mild obesity. (Ludwig, et al., 2001. *J. Clin. Invest.* 107, 379-386.)

MCH action is not limited to modulation of food intake as effects on the hypothalamic-pituitary-axis have been reported. (Nahon, 1994. *Critical Rev. in Neurobiol.* 8, 221-262.) MCH can modulate stress-induced release of ACTH. (Nahon, 1994. *Critical Rev. in Neurobiol.* 8, 221-262.)

Several references describe a receptor that is indicated to bind MCH ("MCH1R"). (Chambers, et al., 1999. *Nature* 400, 261-265, Saito, et al., 1999. *Nature* 400, 265-269, Bächner, et al., 1999. *FEBS Letters* 457:522-524, Shimomura, et al., 1999. *Biochemical and Biophysical Research Communications* 261, 622-626.)

SUMMARY OF THE INVENTION

The present invention features viable MCH1R deficient mice. MCH1R deficient mice contain an alteration in one or both MCH1R alleles that substantially reduces expression of a functional MCH1R from the altered allele. Preferably, MCH1R deficient mice are MCH1R −/− knockout mice.

An alteration that "substantially reduces expression" of a functional MCH1R is either (1) an alteration that results in no active MCH1R being produced from the altered allele or (2) an alteration that results in a MCH1R deficient mouse having one or more phenotypes associated with an MCH1R −/− knockout mouse, when the alteration is present in both alleles. Alterations substantially reducing expression of a functional MCH1R include alterations that result in little or no MCH1R expression and alterations producing a MCH1R derivative which is expressed but contains little or no activity.

Phenotypes associated with a MCH1R −/− knockout mouse include: reduced fat mass, increased food consumption when mice are maintained on regular chow, hyperactivity, neuroendocrine abnormalities, increased energy expenditure as measured by indirect calorimetry, reduced respiratory quotient as measured by indirect calorimetry, decreased sensitivity to diet-induced obesity, resistance to the orexigenic effects of intracerebroventricular administration of MCH and resistance to the anorectic effects of intracerebroventricular administration a peptide antagonist of MCH1R.

Thus, a first aspect of the present invention describes a MCH1R deficient mouse whose genome comprises an alteration in one or both MCH1R alleles. The alteration substantially reduces expression of a functional MCH1R from the altered allele.

Another aspect of the present invention describes a method of producing a MCH1R deficient mouse comprising an alteration of a MCH1R allele. The method comprises the steps of:

(a) altering a MCH1R allele in a mouse embryonic stem cell by homologous recombination with a transgene to produce an altered embryonic stem cell;

(b) introducing the altered embryonic stem cell into a mouse blastocyst to produce an altered blastocyst;

(c) introducing the altered blastocyst into a pseudopregnant mouse to produce a pregnant mouse;

(d) allowing the pregnant mouse to produce offspring; and (e) screening the offspring for the presence of an altered MCH1R allele to identify an MCH1R deficient mouse.

Another aspect of the present invention describes a method of producing a MCH1R deficient mouse comprising an altered MCH1R in both alleles. The method comprises the steps of: (a) breeding two mice each comprising an alteration of the MCH1R in one allele to produce offspring; and (b) screening the offspring for the presence of an altered MCH1R in both alleles.

Another aspect of the present invention describes a method of measuring the affect of a compound on a MCH1R deficient mouse. The method involves the steps of providing the compound to the MCH1R deficient mouse, and measuring one or more phenotypes associated with MCH1R activity.

Another aspect of the present invention describes a method of screening for a compound to affect food intake, metabolism, stress, anxiety, fatigue, locomotor activity, circadian rhythm, or sleep. The method comprises identifying an MCH1R active compound able to modulate MCH1R activity using an in vitro assay; and measuring the ability of the MCH1R active compound on food intake, metabolism, stress, anxiety, fatigue, locomotor activity, circadian rhythm, or sleep.

Other features and advantages of the present invention are apparent from the additional descriptions provided herein including the different examples. The provided examples illustrate different components and methodology useful in practicing the present invention. The examples do not limit the claimed invention. Based on the present disclosure the

DETAILED DESCRIPTION OF THE INVENTION

Figure 1:
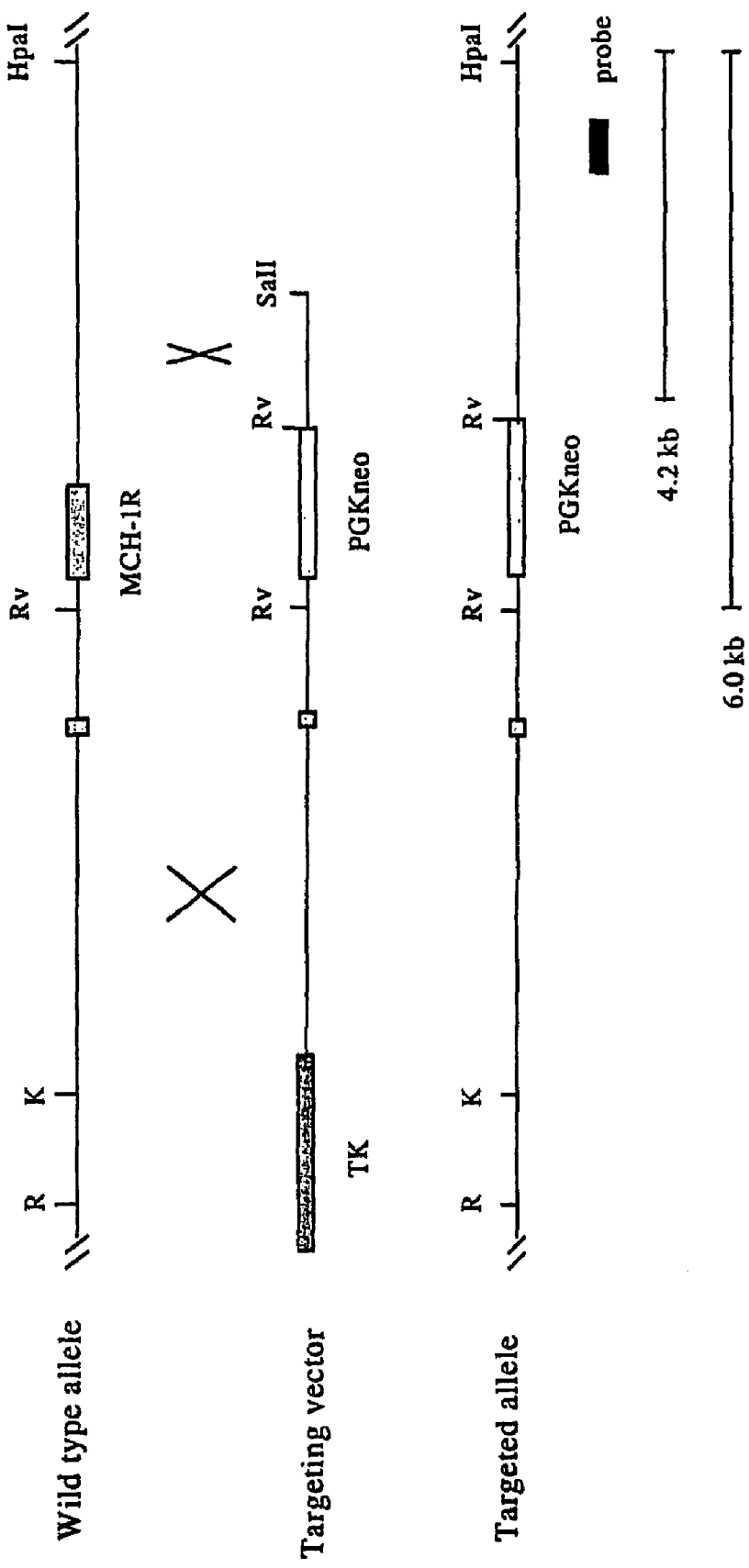
FIG. 1. Strategy employed for disrupting the MCH1R gene. "TK" refers to a HSV-thymidine kinase gene. "PGK-neo" refers to a neomycin resistance gene.

MCH1R deficient mice contain an alteration in one or both MCH1R alleles that substantially reduces expression of a functional MCH1R from the altered allele. The production of MCH1R deficient mice is illustrated by a viable MCH1R −/− knockout mouse where expression of MCH1R is eliminated from both MCH1R alleles. Based on the guidance provided herein concerning the production of such viable MCH1R −/− mice, MCH1R deficient mice containing different types of alterations in one or both MCH1R allele can be produced.

MCH1R deficient mice have a variety of uses such as being used as a tool to examine the physiological roles of MCH1R, to evaluate the ability of compounds to target MCH1R, and to evaluate the ability of compounds to compensate for a deficiency in MCH1R. The ability of compounds to target MCH1R or to compensate for a MCH1R deficiency can be evaluated by measuring changes in one or more phenotypes associated with a MCH1R deficiency.

Studies involving MCH1R mice are preferably performed using mice with an alteration in both MCH1R alleles. Mice containing an alteration in one allele are preferably used as an intermediate animal in the initial production of mice having alterations in both alleles. Propagation of mice with an alteration in both alleles is preferably achieved using male and female mice containing alterations in both MCH1R alleles.

Phenotypes observed in MCH1R deficient mice include reduced fat mass, increased food consumption when mice are maintained on regular chow, hyperactivity, neuroendocrine abnormalities, increased energy expenditure as measured by indirect calorimetry, reduced respiratory quotient as measured by indirect calorimetry, decreased sensitivity to diet-induced obesity, resistance to the orexigenic effects of intracerebroventricular administration of MCH and resistance to the anorectic effects of intracerebroventricular administration of a peptide antagonist of MCH1R.

The observed phenotypes of MCH1R deficient mice point to additional phenotypes associated with energy metabolism alterations. Such additional phenotypes include one or more of the following: increased muscle mass; altered glucose or insulin tolerance, as for instance measured by an oral glucose tolerance test or an intraperitoneal insulin tolerance test; altered sensitivity to intracerebroventricularly administered peptide and non-peptide agonists and antagonists of MCH1R and of other energy expenditure pathways; and altered responsiveness to modulation of food intake pathways and pathways affecting other aspects of energy expenditure.

MCH1R deficient mice with different alterations can have varying degrees of phenotypes associated with a MCH1R −/− knockout mouse. In different embodiments, using techniques described in the Examples below, mice with an MCH1R deficiency consume approximately 12% to approximately 16% more food than MCH1R wild-type mice, and MCH1R deficient mice have approximately a 2-fold increase in dark phase ambulatory activity compared to wild-type mice.

Production of MCH1R Deficient Mice

Based on the guidance provided herein, different types of MCH1R deficient mice can be produced. A preferred scheme for producing MCH1R deficient mice involves producing male and female mice with an altered MCH1R allele and breeding the mice to produce mice having alterations in both alleles.

Techniques for producing mice with an altered genome are well known in the art. (Ausubel, Chapter 23, Manipulating the Mouse Genome, *Current Protocols in Molecular Biology*, John Wiley, 2001). An example of a scheme for producing a mouse with an altered MCH1R allele involves the following:

(a) altering the MCH1R allele in a mouse embryonic stem cell by homologous recombination with a transgene to produce an altered embryonic stem cell;

(b) introducing the altered embryonic stem cell into a mouse blastocyst to produce an altered blastocyst;

(c) introducing the altered blastocyst into a pseudopregnant mouse to produce a pregnant mouse;

(d) allowing the pregnant mouse to produce offspring; and (e) screening the offspring for the presence of an altered MCH1R allele to identify a MCH1R deficient mouse.

Genetic elements involved in gene expression include transcription and translation elements such as a promoter, transcription factor binding sites, splicing sites, polyadenylation region, and ribosome binding site. Removing or altering these elements will decrease or eliminate the production of MCH1R from the MCH1R gene.

MCH1R structural gene alterations can be used to produce an MCH1R derivative having little or no MCH1R activity. A preferred alteration to the MCH1R structural gene involves deleting substantially all of the gene.

A deletion in an MCH1R allele can be accompanied by an insertion of additional nucleic acid. Additional nucleic acid that may be inserted includes nucleic acid encoding a selectable marker having an independent promoter and nucleic acid encoding a reporter protein transcriptionally coupled to the MCH1R promoter. Examples of reporter protein that can be used in chimeric mice are β-galactosidase (lacZ) and green fluorescent protein (GFP) and its derivatives.

Initial alterations are preferably produced using a transgene containing one or more selectable makers and nucleic acid targeting MCH1R for insertion by homologous recombination. Homologous recombination can be performed to create alterations in MCH1R and/or remove MCH1R regions. Markers can be used to facilitate screening for the insertion into a mouse genome, for the insertion occurring by homologous recombination (Ausubel, Chapter 23, Manipulating the Mouse Genome, *Current Protocols in Molecular Biology*, John Wiley, 2001), and for evaluating mRNA localization and expression.

A transgene used for homologous recombination may contain recombinase systems, which may be employed to excise inserted nucleic acid. Examples of recombinase systems include the bacteriophage recombinase Cre/loxP system and the yeast recombinase Flp/FRT system. (Ausubel, Chapter 23, Manipulating the Mouse Genome, *Current Protocols in Molecular Biology*, John Wiley, 2001, and U.S. Pat. No. 5,564,182.) loxP recognition sites can be positioned 3' and 5' of a region to be removed and excised by Cre recombinase. Similarly, frt recognition sites can be positioned 3' and 5' of a region to be removed and excised by Flp recombinase.

Screening for mice containing an altered MCH1R allele can be achieved using techniques such as those measuring the production of MCH1R mRNA transcripts and whether any produced MCH1R transcript is different from wild-type transcript. Techniques for measuring MCH1R mRNA transcripts and the type of transcript include nucleic acid hybridization analysis such as a northern blot analysis which can detect the production and size of transcripts with the use of smaller nucleic acid probes specific for a particular sequence. Polymerase chain reaction PCR) or in situ hybridization can also be employed to measure MCH1R mRNA transcripts.

Whether or not a particular alteration substantially reduces expression of a functional MCH1R can be determined by producing mice containing such alterations in both alleles. The phenotype of mice containing the alteration in both alleles is determined by comparing the phenotypes of MCH1R −/− knockout mice and MCH1R wild-type mice.

Assays Involving MCH1R Mice

Assays involving MCH1R deficient mice can be performed to measure the effect of a compound on a MCH1R deficiency. Such assays can be performed for different purposes such as evaluating the ability of a compound to compensate for a MCH1R deficiency and evaluating the ability of a compound to selectively act at MCH1R.

The effect of a compound on MCH1R deficiency in vivo can be evaluated by measuring one or more phenotypes associated with MCH1R. Techniques for measuring different activities such as food consumption, body weight, stress, anxiety, locomotor activity, sleep, fatigue, circadian rhythm, and energy metabolism are well known in the art. (See, for example, Crawley, J. N., What's Wrong with My Mouse, Wiley-Liss, 2000, Chen, et al., 2000. *Trans. Res.* 9, 145-154 and Chen, et al., 2000. *Nat. Genetics* 26, 97-102.) Examples of techniques for measuring some these different activities are described in the Examples provided below.

In different embodiments, compounds administered to MCH1R deficient mice have previously been identified as MCH1R or MCH2R active compounds using an in vitro assay. MCH2R is another receptor that binds MCH. MCH1R and MCH2R active compounds modulate activity of either or both MCH1R and MCH2R, and include agonists, antagonists, and allosteric modulators.

The ability of a compound to affect in vitro MCH1R or MCH2R activity can be determined using a cloned receptor and measuring receptor activity. The amino acid and encoding cDNA sequences for human MCH1R and MCH2R are provided by SEQ. ID. NOs. 1-4. SEQ. ID. NOs. 1 and 2 provide the amino acid and encoding cDNA for human MCH1R. SEQ. ID. NOs. 3 and 4 provide the amino acid and encoding cDNA for human MCH2R.

MCH1R and MCH2R are G protein coupled receptors. MCH1R couples to both Gi and Gq, while MCH2R couples to Gq. Coupling of Gi results in the inhibition of adenylate cyclase and subsequent reductions in cAMP levels. Coupling to Gq leads to activation of phospholipase C and subsequent elevation of intracellular $Ca^{2+}$.

Recombinantly expressed receptor can be used to facilitate determining whether a compound is active at that receptor. For example, MCH1R or MCH2R can be expressed by an expression vector in a cell line such as HEK 293, COS 7, and CHO not normally expressing the receptor, where the same cell line without the expression vector or with an expression vector not encoding the receptor can act as a control.

Techniques for measuring different G-protein activities, such as Gi, Gs, and Gq are well known in the art. Gi and Gs activity can be measured using techniques such as a melonaphore assay, assays measuring cAMP production, assays measuring inhibition of cAMP accumulation, and assays measuring binding of $^{35}$S-GTP. cAMP can be measured using different techniques such as a radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al., 1993. *Cell Calcium* 14, 663-671, and Feighner, et al., 1999. *Science* 284, 2184-2188.)

Compounds modulating MCH1R activity include agonists, antagonists and allosteric modulators. The ability of a test compound to antagonize MCH1R can be measured by activating the receptor using an MCH1R agonist and measuring the effect of the test compound on MCH1R activity.

MCH1R and MCH2R active compounds have therapeutic applications. Such applications include the ability to achieve one or more of the following: weight loss (e.g., treat obesity), weight gain, treat cancer (e.g., colon or breast), reduce pain, treat diabetes, reduce stress and anxiety, treat locomotor deficits, treat sexual dysfunction, treat fatigue, or treat sleep disorders.

Additional Assays

The increased locomotor activity of MCH1R deficient mice points to associations between MCH1R and stress, anxiety, fatigue, circadian rhythm, and sleep. Compounds affecting stress, anxiety, fatigue, circadian rhythm, or sleep, can be identified using an in vitro MCH1R assay followed by an in vivo assay. The in vivo assay is performed in a mammal such as a mouse, rat, dog, ferret or monkey.

Compounds affecting locomotor activity, stress, anxiety, fatigue, circadian rhythm, or sleep can be used as a research tool and to achieve useful effects in a patient. Useful effects include reducing stress, anxiety or fatigue, and altering sleep patterns. Alteration of sleep patterns is useful to, for example, treat sleep disorders and treat jet lag. Preferably, the patient is human patient. In different embodiments, the ability of a MCH1R active compound that increases MCH1R activity is tested in an in vivo assay that measures a decrease in stress, anxiety or locomotor activity; the ability of a MCH1R active compound that decreases MCH1R activity is tested in an in vivo assay that measures a reduction in fatigue and the ability of a compound to modulate MCH1R activity is tested in an in vivo assay that measures alterations in circadian rhythm or sleep.

EXAMPLES

Examples are provided below to further illustrate different features of the present invention. The examples also illustrate useful methodology for practicing the invention. These examples do not limit the claimed invention.

Example 1

Generation of MCH1R −/− Mice

MCH1R −/− mice were produced using recombinant techniques to obtain MCH1R +/− mice and breeding the MCH1R +/− mice. Production of MCH1R +/− mice involved using an MCH1R targeting vector to disrupt the MCH1R allele in embryonic stem (ES) cells, injecting the transformed ES cells into a blastocyst, implanting the blastocyst into a pseudopregnant female, and identifying MCH1R +/− offspring.

A 14 Kb mouse genomic clone containing MCH1R was obtained from a mouse 129SvJ lambda genomic library (Lambda FIX II Library, Stratagene, La Jolla, Calif.). The clone was identified by screening the library with a 500 bp mouse MCH1R cDNA probe generated from MCH1R by PCR using primers derived from the rat MCH1R sequence. The rat MCH1R sequence is described as the rat SLC-1 in Lakaye, et al., 1988. *Biochim. Biophys. ACTA* 1401:216-220.

The MCH1R targeting vector was made up of two homologous recombination targeting regions, a positive selection element, and a negative selection element (FIG. 1). The two homologous recombination targeting regions were obtained from the mouse genomic clone. One of the regions was a 6.5 Kb 5' MCH1R KpnI to KpnI fragment. The second region was an 1.4 kb 3' MCH1R BamHI to XbaI fragment.

PGKneo was used as the positive selection element and HSV-thymidine kinase was used as the negative selection element. PGKneo provides for neomycin resistance, which serves as a positive selection for integration into the mouse genome. HSV-thymidine kinase provides for sensitivity to acyclovir and its analogs, providing for a negative selection against integration not involving homologous recombination.

Homologous recombination of the targeting vector into the mouse genome was performed by linearizing the targeting vector with NotI and transforming AB2.2 ES cells by electroporation. Electroporation was performed with $1 \times 10^7$ AB2.2 ES cells and 25 μg of vector under standard conditions using a BioRad Gene Pulser (Instruction manual, Lexicon Genetics, The Woodlands, Tex. 77381, Catalog number K100). Transfected cells were then cultured with G418/FIAU for positive and negative selections, respectively. FIAU is the uracil derivative; 2'-fluoro-2'-deoxy-1beta-D-arabinofuranosyl-5-iodo-uracil. Approximately 500 neomycin resistant clones were selected and Southern blot analysis revealed ten correctly targeted ES cell clones in which one of the two MCH1R alleles was successfully replaced by the PGK-neomycin resistance cassette.

The ten ES cell clones were expanded and microinjected into mouse blastocysts. Mouse blastocysts were implanted into a pseduopregnant female mice. (Gene Targeting, a practical approach, Joyner A. L. eds, IRL press, 1993.) The implanted mice were allowed to go to term. Transgenic MCH1R +/− offspring were identified by Southern analyses.

Transgenic MCH1R −/− mice were produced by breeding male and female MCH1R +/− mice. MCH1R −/− mice were produced in the expected Mendelian ratio. The absence of MCH1R alleles was verified by Southern blot and PCR genotyping. MCH1R −/− mice of both sexes are fertile and their growth rates are comparable to that of wild-type littermate controls out to approximately 20 weeks of age. MCH1R −/− mice greater than approximately 20 weeks of age exhibit slightly, but significantly, lower body weights as compared to wild-type littermate mice.

PCR genotyping was performed using a Qiagen HotStart PCR kit following the Qiagen protocol. Three different oligonucleotide primers were used to distinguish the knockout allele from the wild-type allele. MCH-5L2 (SEQ. ID. NO. 5): 5'-AAA TTG CTA GGG AGG CTT GCA G-3': neo-5 (SEQ. ID. NO. 6): 5'-TAA AGC GCA TGC TCC AGA CTG CCT T-3': MCH-3t (SEQ. ID. NO. 7): 5'-TTA AAG GAA CCC AAG CTA GGC ACC-3'. Primer pair MCH-5L2 and MCH-3t generates a 190 bp fragment from the wild-type MCH1R allele, while primer pair neo-5 and MCH-3t generates a 260 bp fragment from the disrupted MCH1R allele.

Southern blot analysis was preformed using a 3' probe and a coding region probe. (Sambrook, et al., Molecular Cloning, a Laboratory Manual, $2^{nd}$ ed. 1989). The 3' flanking probe is a 0.95 kb PCR fragment located 180 bp 3' of the short arm of the targeting vector. Upon EcoRV-HpaI digestion, the probe detects a 6.0 kb band from the wild-type MCH1R allele, and a 4.2 kb band from the mutant allele (FIG. 1).

The coding region probe is a 1.1 kb Kpn-BamHI fragment covering a portion of the MCH1R coding region, including the first transmembrane domain to the stop codon. The coding region probe also detects a 6.0 kb wild-type band on EcoRV-HpaI digested genomic DNA, but detects no signal from the knocked out allele.

Mouse cDNA encoding for MCH1R and the mouse MCH1R sequences are provided by SEQ. ID. NOs. 10 and 11. SEQ. ID. NO. 10 provides the cDNA sequence. SEQ. ID. NO. 11 provides the amino acid sequence.

Example 2

In Situ Hybridization

In situ hybridization was performed to verify the absence of MCH1R mRNA in the brain of MCH1R −/− mice. MCH1R −/− and age/sex matched wild-type control mice were killed by decapitation, and brains were quickly removed and frozen in −40° C. isopentane, and stored at −80° C. until use. Coronal brain sections (14 μM) were cut at −17° C. with a cryostat microtome and thaw-mounted onto baked microslides. Following fixation in ice-cold 4% phosphate-buffered paraformaldehyde, the tissue sections were stored in 95% ethanol at 4° C. until use.

Hybridization was performed using hybridization probes that consist of an equal molar mixture of two non-overlapping, antisense oligonucleotides against the coding region of MCH1R:

Oligo 407 (SEQ. ID. NO. 8):
5'-CTAATGAACGAGAGAGCCCACAGGAG-GCAGATCACCAGGGTGGCC-3'

Oligo 408 (SEQ. ID. NO. 9):
5'-CCAGCACACAAAGAAGACCAGACAGATG-GCAATGGCTGTGCGGGT-3'.

The probes were terminally labeled with [$\alpha$-$^{33}$P]dATP and terminal transferase, and hybridization and washing conditions were as described in Guan, et al., 1998. *Mol. Brain Res.* 59, 273-279. mRNA transcripts were observed in wild-type mice, but not in MCH1R −/− mice.

Example 3

Evaluation of Body Composition

Evaluations of body composition were preformed using 5-7-month-old male and female MCH1R +/+, MCH1R +/−, and MCH1R −/− littermate mice. Body composition was analyzed by dual energy x-ray absorptiometry (DEXA; QDR 4500, Hologic, Inc.), using the QDR 4500 Small Animal Studies software version 9.0.

Figure 2A:
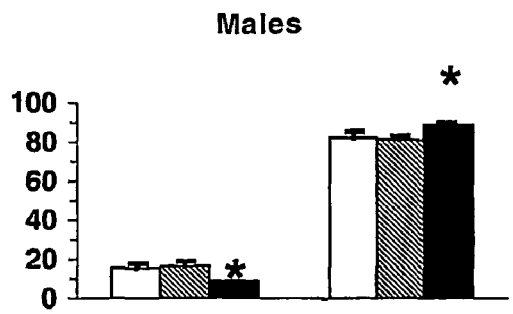
FIG. 2. DEXA analysis of 5-7-month-old group-housed male and female MCH1R +/+ (white bars), MCH1R +/− (hatched bars) and MCH1R −/− (shaded bars; n=12-14 per group) littermate mice. All P values are from comparisons between MCH1R +/+ and MCH1R −/− littermates. **P<0.01, *P<0.05.
Figure 2B:
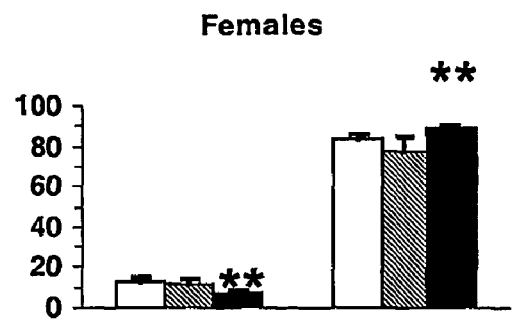

DEXA revealed that both male and female 5-7-month-old MCH1R −/− mice were significantly leaner than wild-types (FIG. 2). Both genders of MCH1R −/− mice possessed ~50% less fat mass and ~7% more lean mass than wild-types. Male and female MCH1R +/− mice exhibited normal body composition. Evaluation of a subset of individual fat pads and DEXA analysis of individually-housed animals from the second line corroborated the lean phenotype.

Example 4

Food Intake Measurement

Food intake measurements were preformed using male and female MCH1R +/+. MCH1R +/−, and MCH1R −/− mice. The mice were separated into individual microisolator cages at approximately one month of age and at least seven days prior to the initiation of any experiment.

Regular mouse chow (Teklad 7012; 5% fat, 19% protein, and 5% fiber; 3.41 grams/kcal and 14.8% kcal from fat) was provided to 9.5-10-week-old mice as pellet food in wire cage tops containing food hoppers. Food was weighed daily for 4 days. Food intake reported as the average food consumed per mouse per day over the course of the four-day period is shown in Table 1.

TABLE 1

Daily Food Consumption of Male and Female MCH1R Mice

| Gender and Genotype | Daily Food Consumption (g/mouse/day) Mean ± SEM | n value | P value |
|---|---|---|---|
| Male MCH1R +/+ | 4.18 ± 0.14 | 11 | |
| Male MCH1R +/− | 4.26 ± 0.12 | 10 | |
| Male MCH1R −/− | 4.84 ± 0.18*# | 11 | *, <0.02 vs. +/+; #, <0.02 vs. +/− |
| Female MCH1R +/+ | 4.06 ± 0.16 | 10 | |
| Female MCH1R +/− | 3.70 ± 0.44* | 4 | |
| Female MCH1R −/− | 4.56 ± 0.15*# | 8 | *, <0.04 vs. +/+; #, <0.04 vs. +/− |

Both male and female MCH1R −/− mice are significantly hyperphagic. Male and female MCH1R −/− mice consumed approximately 16% and 12% more food, respectively, than wild-type control mice.

Example 5

Assessment of Ambulatory Activity and Fine Movements

Ambulatory activity and fine movement studies were preformed using MCH1R +/+, MCH1R +/− and MCH −/− mice. The locomotor activity of male MCH1R +/+, MCH1R +/−, and MCH1R −/−, and female MCH1R +/+, MCH1R +/− and MCH1R −/− 8-9-week-old littermate mice was examined using a cage rack Photobeam Activity System (San Diego Instruments). Mice were housed individually in transparent plexiglass cages (40×20×20 cm) for several weeks prior to evaluation.

The results of the ambulatory activity and fine movement studies are shown in Tables 2 and 3. During examination two consecutive photobeam breaks occurring in adjacent photobeams was scored as ambulatory movement. Two or more consecutive photobeam breaks occurring in the same photobeam, with no other photobeams being interrupted, was scored as fine movements. The total number of ambulatory movements in a given part of the light cycle multiplied by the distance between two adjacent photobeams (0.053975 m) equaled the total distance traveled during that given part of the light cycle. MCH1R −/− mice of both sexes exhibit approximately a 2-fold increase in dark phase ambulatory activity.

TABLE 2

Ambulatory Activity of Male and Female MCH1R Mice

| Gender and Genotype | Ambulatory Activity (meters traveled) Mean ± SEM Light phase | Dark phase | N value | P value Light phase | Dark phase |
|---|---|---|---|---|---|
| Male MCH1R +/+ | 31.20 ± 6.49 | 114.35 ± 16.38 | 11 | | |
| Male MCH1R +/− | 19.19 ± 4.61 | 98.73 ± 7.26 | 6 | | |
| Male MCH1R −/− | 49.74 ± 6.09*# | 223.70 ± 29.32*# | 11 | *, = 0.05 vs. +/+; #, <0.004 vs. +/− | *, <0.005 vs. +/+; #, <0.008 vs. +/− |
| Female MCH1R +/+ | 29.39 ± 6.37 | 105.52 ± 11.93 | 10 | | |
| Female MCH1R +/− | 64.03 ± 21.14 | 100.23 ± 17.30 | 4 | | |
| Female MCH1R −/− | 57.55 ± 13.41* | 209.81 ± 19.64*# | 8 | *, = 0.06 vs. +/+ | *, <0.001 vs. +/+; #, <0.006 vs. +/− |

TABLE 3

Fine Movements of Male and Female MCH1R Mice

| Gender and Genotype | Fine Movements (number of beam breaks) Mean ± SEM Light phase | Dark phase | N value | P value Light phase | Dark phase |
|---|---|---|---|---|---|
| Male MCH1R +/+ | 707.18 ± 124.07 | 1619.84 ± 243.26 | 11 | | |
| Male MCH1R +/− | 865.50 ± 58.70 | 1703.33 ± 108.86 | 6 | | |
| Male MCH1R −/− | 889.36 ± 122.11 | 2672.54 ± 270.36*# | 11 | | *, <0.01 vs. +/+; #, <0.03 vs. +/− |
| Female MCH1R +/+ | 1034.4 ± 121.27 | 1969.25 ± 89.01 | 10 | | |
| Female MCH1R +/− | 1209.25 ± 234.84 | 2098.75 ± 472.62 | 4 | | |
| Female MCH1R −/− | 1178.75 ± 163.29 | 2429.00 ± 88.16* | 8 | | *, <0.005 vs. +/+ |

Example 6

Assessment of Metabolic Rate and Respiratory Quotient

Metabolic rate and respiratory quotient were evaluated by indirect calorimetry using MCH1R +/+ and MCH −/− mice. The locomotor activity of male MCH1R +/+ and MCH1R −/− 12-week-old littermate mice was examined using a 16-chamber open-circuit Oxymax system (Columbus Instruments). Mice were housed individually in transparent plexiglass cages (40×20×20 cm) for several weeks prior to evaluation.

Figure 3:
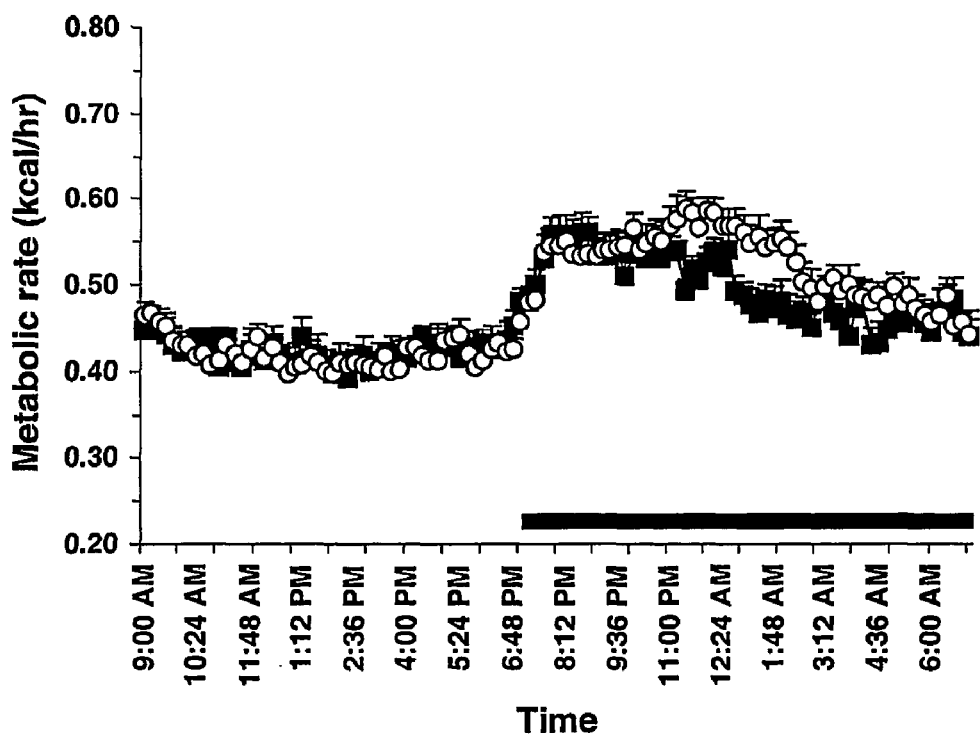
FIG. 3. Metabolic rate of ~8-week-old individually-housed male MCH1R +/+ (n=10; filled squares) and MCH1R −/− (n=13; open circles) littermates. From 10 PM to 5 AM, the MCH1R −/− curve was significantly different (P<0.05) from the MCH1R +/+ curve. The solid horizontal bar represents the dark phases of the study.
Figure 4:
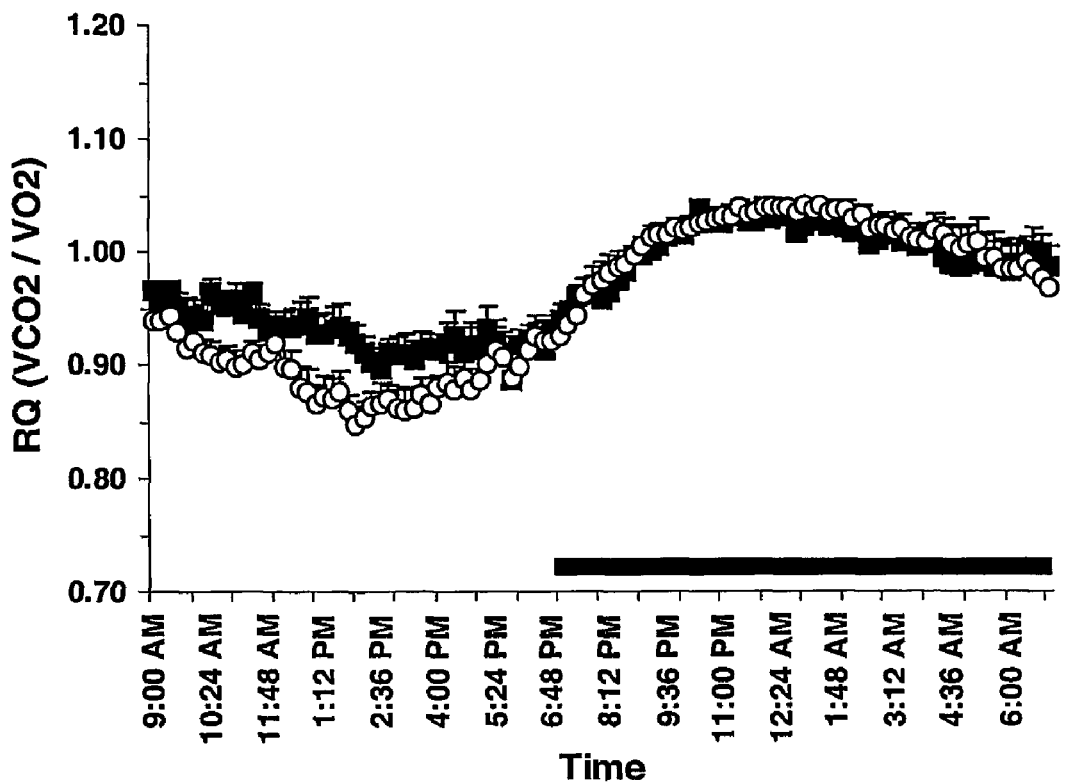
FIG. 4. Respiratory quotient (RQ) of mice in FIG. 3. The MCH1R −/− curve was significantly different (P<0.01) from the MCH1R +/+ curve for the entire light phase. The solid horizontal bar represents the dark phases of the study.

MCH1R −/− mice exhibited a significantly greater metabolic rate during a portion of the dark phase of the light-dark cycle (FIG. 3) that was temporally correlated with the period of hyperactivity, suggesting that this increase in metabolic rate is secondary to the hyperactivity. The respiratory quotient, an indicator of metabolic fuel preference, was significantly lower in male MCH1R −/− mice during the light phase, but was indistinguishable from that of wild-types during the dark phase (FIG. 4), implying that MCH1R −/− mice rely upon the oxidation of free fatty acids and less upon glycolysis during periods when they are not actively eating.

Example 7

Assessment of Neuroendocrine Profile

Neuroendocrine profiles were evaluated in male and female MCH1R +/+ and MCH −/− littermate mice. Plasma leptin, insulin, total T4 and corticosterone levels were measured by RIA. Plasma glucose and triglyceride levels were measured by enzyme-colorimetric assays (Sigma and Roche, respectively).

Plasma glucose, insulin and triglyceride levels were not significantly different in 5-7-month-old MCH1R −/− and wild-type littermates of either gender (Table 4). Plasma leptin and total thyroxine (T4) levels were significantly lower in male Mch1r$^{-/-}$ mice relative to wild-types, and female levels revealed similar trends (Table 4). Lower leptin levels are consistent with the lean phenotype and lower T4 levels support the notion that MCH may be involved in the regulation of thyroid function (Kennedy, et al., 2000. *Endocrinology* 142:3265-3268). Alternatively, alterations in T4 levels may reflect a compensatory response to the increased energy expenditure. Plasma corticosterone levels were significantly greater in 6-7-month-old male Mch1r$^{-/-}$ mice relative to wild-type littermates (Table 4). This is consistent with the finding that MCH administration reduces basal and stress-induced plasma ACTH levels in rats (Bluet-Pajot, et al., 1995. *J. Neuroendocrinol.* 7:297-303), and suggests that MCH1R may be involved in the regulation of adrenal function.

TABLE 4

Neuroendocrine Profiles of Male and Female MCH1R Mice.

| | Males | | Females | |
|---|---|---|---|---|
| | MCH1R +/+ | MCH1R −/− | MCH1R +/+ | MCH1R −/− |
| Leptin (ng/ml) | 6.05 ± 1.99 | 2.12 ± 0.08* | 3.87 ± 0.92 | 2.31 ± 0.06 |

TABLE 4-continued

Neuroendocrine Profiles of Male and Female MCH1R Mice.

|  | Males | | Females | |
| --- | --- | --- | --- | --- |
|  | MCH1R +/+ | MCH1R −/− | MCH1R +/+ | MCH1R −/− |
| Triglyceride (mg/dl) | 77 ± 10 | 69 ± 6 | 57 ± 7 | 64 ± 5 |
| Insulin (ng/ml) | 0.61 ± 0.15 | 0.57 ± 0.12 | 0.31 ± 0.04 | 0.33 ± 0.04 |
| Glucose (mg/dl) | 140 ± 7 | 137 ± 5 | 132 ± 5 | 123 ± 4 |
| T4 (µg/dl) | 5.35 ± 0.25 | 4.32 ± 0.23* | 4.58 ± 0.37 | 4.05 ± 0.22 |
| Corticosterone (ng/ml) | 9 ± 1.1 | 23.6 ± 5.4* | ND | ND |

Plasma leptin, triglyceride, insulin, glucose and total thyroxine (T4) levels of group-housed male and female 5–7-month-old MCH1R littermate mice (n = 10–14 per group).
Plasma corticosterone levels of individually-housed 6–7-month-old male MCH1R littermate mice (n = 9–10 per genotype) maintained in isolation and fed ad libitum.
*$P \leq 0.05$;
ND, not determined.

Example 8

Assessment of Neuropeptide Expression

Corticotrophin-releasing factor (CRF) mRNA levels in the brain were measured by in situ hybridization. CRF mRNA levels in the paraventricular nucleus of the hypothalamus (PVN) were significantly lower in male MCH1R −/− mice relative to wild-types, yet were normal in the central nucleus of the amygdala (CEA) (PVN: MCH1R −/−, 79.5±9.6 Ci/g tissue; MCH1R +/+, 105.3±10.1 Ci/g tissue; P<0.05; CEA: MCH1R −/−, 57.5±1.3 Ci/g tissue; MCH1R +/+, 57.0±5.9 Ci/g tissue; n=5 per genotype). This suggests that the elevated corticosterone levels are not due to increased hypothalamic CRF. Instead, it is likely that the reduced CRF expression in the PVN is a consequence of negative feedback driven by the elevated levels of corticosterone. In contrast to CRF, hypothalamic levels of neuropeptide Y (NPY), agouti-related protein (AgRP), galanin, pro-opiomelanocortin, and cocaine- and amphetamine-regulated transcript mRNAs measured during the light phase were all normal in MCH1R −/− mice.

Example 9

Assessment of Responsiveness to Diet-induced Obesity

Figure 5:
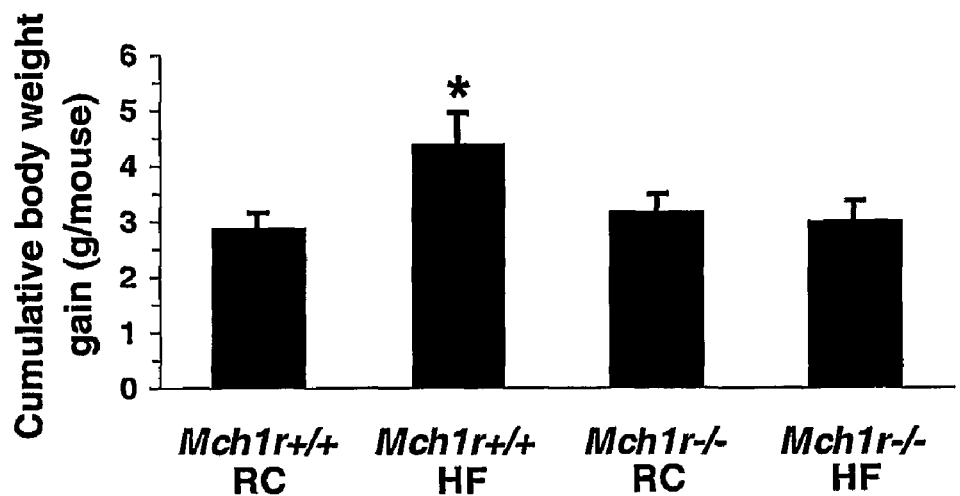
FIG. 5. Cumulative body weight gains of female wild-type (Mch1r$^{+/+}$) and Mch1r$^{-/-}$ littermates maintained simultaneously on either a regular chow diet (RC) or a high fat diet (HF) for 7 weeks (n=9-12 per group). All groups were weight matched and all mice were 6-8-weeks-old at the initiation of the study.
Figure 6:
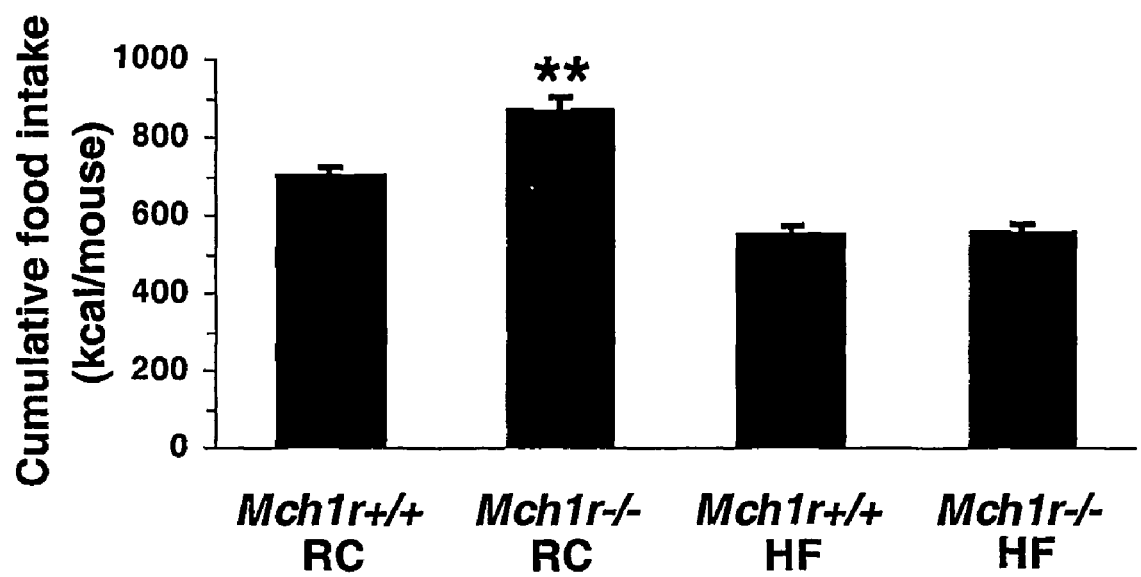
FIG. 6. Cumulative food intake by mice in FIG. 5 during the 7-week period (n=9-11 per group). P values are from comparisons between chow and high fat groups of the same genotype (*) or between Mch1r$^{+/+}$ and Mch1r$^{-/-}$ littermates maintained on the same diet (**). *P<0.05, **P<0.001.

Female wild-type mice maintained on a high fat diet for seven weeks gained significantly more body weight than wild-type littermates maintained on regular chow (FIG. 5). In contrast, female MCH1R −/− mice maintained on the high fat diet gained the same amount of body weight as MCH1R −/− littermates maintained on regular chow. This decreased susceptibility to diet-induced obesity is most likely a consequence of the hyperactivity and associated increase in energy expenditure. Interestingly, maintenance on the high fat diet abolished the significant hyperphagia (24.3%) observed with maintenance on regular chow (FIG. 6).

Example 10

Assessment of Responsiveness to Centrally Administered Orexigenics

Figure 7:
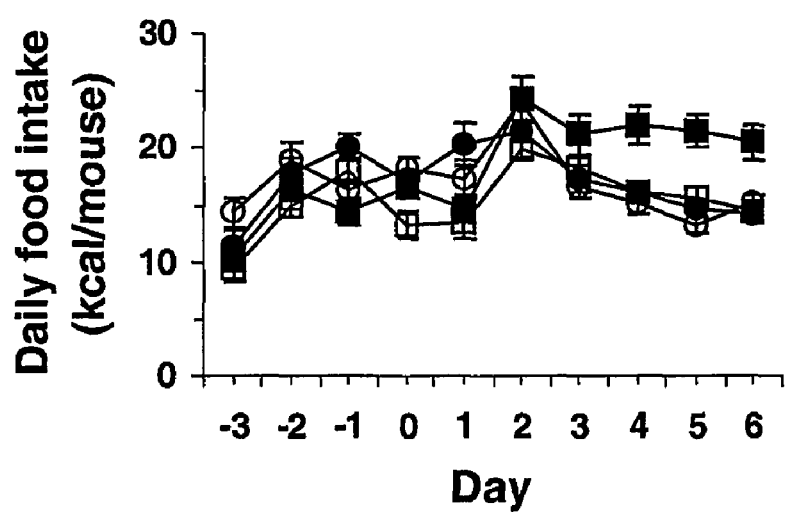
FIG. 7. Effect of chronic MCH infusion on daily food intake. Male 11-13-week-old MCH1R +/+ (squares) and MCH1R −/− (circles) littermates received chronic dorsal third ventricle infusions of either MCH (~12 nmole/mouse/day; filled symbols) or vehicle (open symbols) for 6 days (n=9-11 per group). Mice were cannulated and implanted with osmotic pumps containing only vehicle on day −5. On day 0, original pumps were replaced with new pumps containing either vehicle or MCH dissolved in vehicle. Beginning on day 1, all mice were maintained on a moderate fat diet. From days 1 to 6, the MCH1R +/+, MCH-treatment curve was significantly different (P<0.005) from the three other curves.
Figure 8:
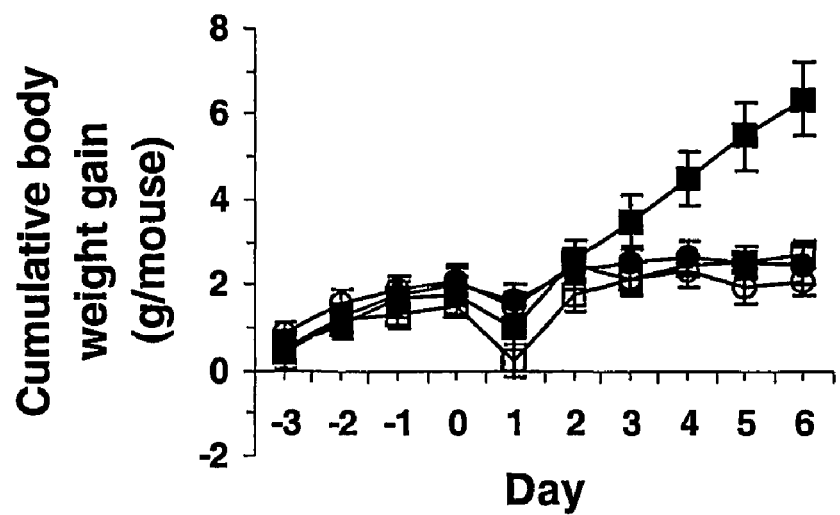
FIG. 8. Effect of chronic MCH infusion on cumulative body weight gain. Body weights of mice in FIG. 7 were measured daily and values from day −4 were used to calculate cumulative body weight gains. From days 1 to 6, the MCH1R +/+, MCH-treatment curve was significantly different (P<0.0001) from the three other curves.
Figure 9:
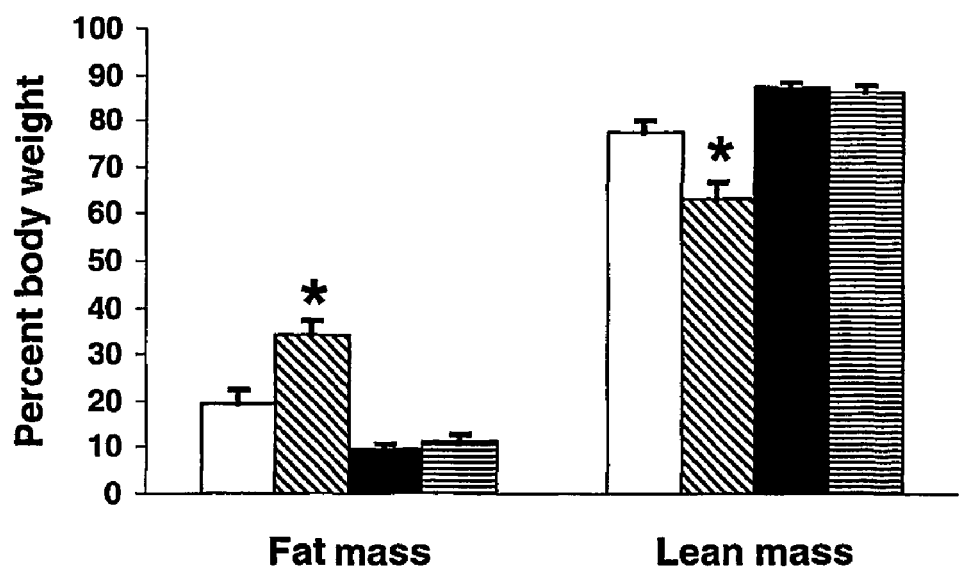
FIG. 9. Effect of chronic MCH infusion on body composition. DEXA analysis of body composition was performed on mice in FIG. 7 at the end of the 6-day chronic infusion period MCH1R +/+: vehicle, white bars; MCH, hatched bars; MCH1R −/−: vehicle, shaded bars; MCH, striped bars). P values are from comparisons between treatment groups of the same genotype (*) or between genotypes of the same treatment (**). *P<0.005, **P<0.01.

MCH1R −/− mice exhibited normal responses to both acute left lateral and dorsal third ventricle administrations of NPY and AgRP, demonstrating that MCH1R is not required for their orexigenic actions. Additionally, these data suggest that the hyperphagia is not a consequence of heightened NPY or AgRP signaling. Acute administrations of MCH were without significant effects, but tended to increase the food intake of only wild-types. Subsequently, the responses of MCH1R −/− and wild-type littermates to chronic dorsal third ventricle infusions of MCH were evaluated. Six days of chronic MCH treatment resulted in significantly greater food intake (FIG. 7), body weight gains (FIG. 8) and altered body composition (FIG. 9) in wild-types, while MCH1R −/− littermates were not affected, demonstrating that MCH1R is required for the orexigenic actions of MCH.

Other embodiments are within the following claims. While several embodiments have been shown and described, various modifications may be made without departing from the spirit and scope of the present invention.

What is claimed is:

1. A transgenic mouse whose genome comprises a homozygous disruption in it's melanin concentrating hormone type 1 receptor (MCH1R) gene, wherein said disruption results in one or more phenotypes selected from the group consisting of: hyperphagia, reduced fat mass, increased lean mass, increased ambulatory activity and increased fine movements.

2. The transgenic mouse of claim 1, wherein said mouse comprises each of said phenotypes.

3. A method of measuring the affect of a compound on MCH1R deficiency comprising the steps of providing said compound to the mouse of claim 1, and measuring the affect of said compound on one or more phenotypes associated with MCH1R deficiency.

4. The method of claim 3, wherein said method comprises measuring hyperphagic or hypophagic activity.

5. The method of claim 3, wherein said method comprises measuring a change in fat mass.

6. The method of claim 3, wherein said method comprises measuring a change in muscle mass.

7. The method of claim 3, wherein said method comprises measuring increased or decreased locomotor activity.

8. The method of claim 3, wherein said method comprises measuring increased or decreased fine motor movements.

9. The method of claim 3, wherein said phenotype is an increased or decreased metabolic indicator selected from the group consisting of: oxygen consumption, carbon dioxide production, metabolic rate, pseudo-resting metabolic rate, respiratory exchange ratio and respiratory quotient.

10. The method of claim 3, wherein said compound is active at MCH2R.

* * * * *